United States Patent [19]

Hayashi et al.

[11] Patent Number: 5,424,055
[45] Date of Patent: Jun. 13, 1995

[54] ULTRAVIOLET SCREENING COMPOSITED OXIDE AND PROCESS FOR PRODUCING THE SAME

[75] Inventors: Takao Hayashi; Norihiro Sato, both of Shimonoseki; Hosoi, Manabu, Oomiya; Nobuyoshi Kasahara, Sayama; Katsuhiko Yoshimaru, Tokyo, all of Japan

[73] Assignee: Mitsui Mining & Smelting Co., Ltd., Tokyo, Japan

[21] Appl. No.: 34,709

[22] Filed: Mar. 22, 1993

[30] Foreign Application Priority Data

Mar. 23, 1992 [JP] Japan .................. 4-094968

[51] Int. Cl.$^6$ .................. A61K 7/42; A61K 31/28; C01G 9/02
[52] U.S. Cl. .................. 423/622; 424/59; 514/498; 514/614; 514/642; 514/951
[58] Field of Search .................. 424/59; 423/622; 514/498, 614, 642, 957

[56] References Cited

U.S. PATENT DOCUMENTS

| | | | |
|---|---|---|---|
| 5,089,248 | 2/1992 | Akhtar | 423/622 |
| 5,093,099 | 3/1992 | Haishi et al. | 423/622 |

FOREIGN PATENT DOCUMENTS

| | | | |
|---|---|---|---|
| 006266 | 6/1981 | Japan | 423/622 |
| 2260716 | 11/1987 | Japan | 423/622 |
| 2275025 | 11/1987 | Japan | 423/622 |
| 2275182 | 11/1987 | Japan | 423/622 |
| 0317272 | 3/1989 | Japan | 423/622 |
| 2059425 | 2/1990 | Japan | 423/622 |
| 3183620 | 8/1991 | Japan | 423/622 |
| 3223111 | 10/1991 | Japan | 423/622 |

*Primary Examiner*—Dale R. Ore
*Attorney, Agent, or Firm*—Bucknam and Archer

[57] ABSTRACT

The composite oxide comprises, by weight, 100 parts of zinc oxide and at least one member, incorporated therein, selected from seven specific oxides in their specific amounts such as 0.001 to 5.0 parts of lanthanum oxide, 1.0 to 10.0 parts of cobalt oxide, 1.0 to 30.0 parts of titanium oxide, the composite oxide being surface treated with a silicone oil or a fatty acid to provide a surface-treated composite oxide of the present invention which has excellent ultraviolet screening capability and high visible light transmittance, these superior properties being well balanced with each other, and can maintain said superior properties over a long period of time. In one embodiment, there is provided a process for producing the ultraviolet screening surface-treated composite oxide.

9 Claims, No Drawings

ULTRAVIOLET SCREENING COMPOSITED OXIDE AND PROCESS FOR PRODUCING THE SAME

BACKGROUND OF THE INVENTION

1. [Field of the Invention]

The present invention relates to an ultraviolet screening composite oxide and a process; for producing the same. More particularly, the present invention relates to a white ultraviolet screening composite oxide which is used in the preparation of paints, inks, cosmetics and the like, excellent in the capability of screening ultraviolet rays, highly visible-light transmittable and excellent in storage stability.

2. [Prior Art]

Ultraviolet rays having a wavelength of 320 to 400 nm get the skin sunburnt and are causative of melanism, inflammation, etc. Further, the ultraviolet rays often decompose a matrix resin contained in paints and cosmetics, decompose or fade a pigment, or oxidize fats and oils and perfume to bring about the deterioration and change of flavor thereof.

For this reason, an attempt to solve these problems has been made through the use of an ultraviolet screening material. An ultraviolet screening material of this type known in the art is ultrafine titanium oxide. Although titanium oxide exhibits an excellent screening effect in the region of ultraviolet rays, it is poor in transmittance in the region of visible lights because the refractive index (2.61 to 2.90 in the rutile form) of titanium oxide is larger than that (2.00 to 2.02) of zinc oxide. For this reason, the incorporation of titanium oxide in transparent materials, such as paints and cosmetics, causes them to turn opaque white in color. Further, titanium oxide is disadvantageous because it is liable to deteriorate the matrix upon being exposed to ultraviolet rays as compared with zinc oxide.

It is reported that ultrafine zinc oxide may be used as another screening material. Specifically, Japanese Patent Appln. Laid-Open Gazette No. Hei. 2-208369 (208369/90) proposes the use of ultrafine zinc oxide having a specific surface area of 20 m$^2$/g or more as an ultraviolet screening material, and makes mention of the screening effect in the ultraviolet region and the transmittance in the visible region. Even when such an ultrafine zinc oxide having a large specific surface area was used, the transmittance in the visible region was unsatisfactory.

Japanese Patent Appln. Laid-Open Gazette No. Sho. 62-275182 (275182/87) disclose an ultraviolet screening material (or agent) composed of a composite metal oxide in which the metal is aluminum, iron or the like and zinc. This ultraviolet screening material exhibits excellent ultraviolet screening capability and high visible light transmittance. However, although this screening material is superior in such screening capability and transmittance as above at its initial stage, it will subsequently raise a problem as to its superior properties being deteriorated with time thereby making its storage stability inferior. Accordingly, the above ultraviolet screening material raises a problem that it cannot satisfactorily be used over a long period of time and is not suited for practical use.

SUMMARY OF THE INVENTION

The present invention has been made with a view to solving the above-described problems of the prior art and an object of the present invention is to provide a white ultraviolet screening material which offers a good balance between excellent ultraviolet screening capability and high visible light transmittance these excellent screening capability and high transmittance being not being deteriorated with the lapse of time, and is excellent in storage stability.

Another objects is to provide a process for producing the white ultraviolet screening material.

The above-described objects can be attained by incorporating a predetermined amount of an oxide of a particular clement as a dopant in zinc oxide to form a composite oxide and then surface treating the thus formed composite oxide with a silicone oil or a fatty acid.

Specifically, the ultraviolet screening composite material of the present invention comprises 100 parts by weight of zinc oxide and at least one member, incorporated therein, selected from among the following oxides (1) to (7):

(1) 0.001 to 5.0 parts by weight of lanthanum oxide,
(2) 0.001 to 5.0 parts by weight of cerium oxide,
(3) 1.0 to 10.0 parts by weight of iron oxide,
(4) 1.0 to 10.0 parts by weight of cobalt oxide,
(5) 1.0 to 10.0 parts by weight of nickel oxide,
(6) 0.1 to 30.0 parts by weight of titanium oxide, and
(7) 0.1 to 30.0 parts by weight of aluminum oxide, to form a composite oxide which is then surface treated with a silicone oil or a fatty acid.

DESCRIPTION OF THE PREFERRED EMBODIMENTS

In the present invention, the ultraviolet screening composite material comprises 100 parts by weight of zinc oxide and at least one member, incorporated therein, selected from among the above-described oxides (1) to (7) to form a composite oxide which is then surface treated with a silicone oil or a fatty acid. The content of the oxide of each of the doping elements based on zinc oxide varies from element to element as mentioned above. When the content of the oxide of each doping element is below the above-described lower limit, the ultraviolet screening effect is small. On the other hand, when the content exceeds the upper limit, the ultraviolet screening effect is saturated and there is unfavorably raised a problem of transparency in the visible light region. In the present invention, it is a matter of course theft two or more oxides selected from the oxides (1) to (7) may be incorporated. In this case, only if the content of at least one oxide is within its range mentioned above the content of the other oxides may be below their range described above. For example, in the case of the incorporation of lanthanum oxide and iron oxide in zinc oxide, when the amount of lanthanum oxide incorporated is 0.001 to 5.0 parts by weight based on 100 parts by weight of zinc oxide, the content of the iron oxide may be less than 1.0 part by weight.

Since the surface of the ultraviolet screening composite oxide of the present invention is very active, it is necessary to treat the surface of the composite oxide with a silicone oil or a fatty acid for the purpose of keeping the storage stability of said oxide and preventing a reaction thereof with the matrix or other additives when the composite oxide is incorporated in paints, cosmetics and the like. Examples of the silicone oil, used for this purpose include dimethylsilicone methylphenylsilicone oil, cyclic silicone oil, polyether silicone oil, modified silicone oil and methylhydrogensilicone oil. Examples of the fatty acid include saturated fatty acids such as n-decanoic acid, caprilic acid, lauric acid, stearic acid, behenic acid and palmitic acid, linolic acid, linolenic acid and oleic acid. The amount of the silicone oil or fatty acid used (coated) is preferably 0.05 to 10% by weight based on the composite oxide.

The process for producing an ultraviolet screening composite oxide according to the present invention comprises separately and simultaneously introducing an acidic solution containing zinc and at least one member selected from lanthanum, cerium, iron, cobalt, nickel, titanium and aluminum and an alkaline solution to a reaction tank and agitating the resulting mixture.

The process of the present invention will now be described in more detail.

At the outset, the above-described at least one doping element is added in a predetermined amount to an aqueous solution of an acidic zinc salt having a zinc concentration of 1 to 5 mol/l to prepare an acidic solution. Separately, a precipitating solution is prepared. A solution of an alkali metal carbonate, a solution of an alkali metal hydroxide and an oxalate compound solution are preferably used as the precipitating solution. The concentration of the precipitating solution is in the range of from 0.1 to 10 mol/l.

The acid solution and the precipitating solution are continuously fed separately from each other to a reaction tank through the use of a flow-rate adjustable pump while maintaining the reaction temperature and pit each at a constant value. In the reaction tank, a coprecipitate comprising zinc and the at least one doping element is formed by neutralization. In the reaction, the flow rate is adjusted so that an equivalent ratio of zinc to the precipitating solution is 1:1 to 1:3. In this case, it is necessary to conduct agitation uniformly at a high rate of 2000 to 20000 rpm. The coprecipitation of the reaction product under the above-described condition makes it possible to stably conduct the operation and prepare a coprecipitate having a stable quality even in case of mass production. Further, the above high-speed agitation serves to instantaneously diffuse the resultant coprecipitate and prevent particles thereof from coarsening or agglomeration, thus promoting the formation of ultrafine particles. In the above-described continuous treatment, a slurry containing a coprecipitate suspended therein is gradually withdrawn, for example, through the bottom of the reaction tank.

The withdrawn slurry containing a coprecipitate suspended therein is subjected to solid-liquid separation, filtration, washing and drying, and then fired for 2 to 3 hrs at a temperature in the range of from 300° to 1000° C., preferably from 350° to 700° C. under atmospheric or reduced pressure (10 mmHg or less).

The composite oxide thus obtained is surface treated with a silicone oil or a fatty acid for keeping its storage stability. This treatment is conducted by dissolving the silicone oil or fatty acid in an organic solvent which is an alcohol such as methanol or ethanol, or a ketone such as acetone or MEK, to obtain a solution and them either directly immersing the composite oxide in the solution or spraying the solution on the composite oxide. Thereafter the composite oxide covered with the solution is dried again at 80° to 150° C.

The surface treated composite oxide of the present invention exhibits the following performances.

(1) It contains specific oxides in respective predetermined amounts and, therefore, it has an ultraviolet screening effect superior to that of the conventional zinc oxide and high transmittance in the region of visible lights.

(2) It will not react with the matrix and additives of paints and cosmetics etc. when it is incorporated in the latter, has improved storage stability and can maintain its excellent ultraviolet screening effect and high transmittance in the visible light region over a long period of time, because it has been surface treated.

PREFERRED EMBODIMENTS OF THE PRESENT INVENTION

The present invention will now be described in more detail with reference to the following Examples and Comparative Examples.

EXAMPLE 1

5075 g (3 kg in terms of zinc oxide) of 99% zinc chloride were dissolved in 9 l of pure water, and 3.13 kg (5% by weight in terms of titanium based on zinc oxide) of 24% titanium sulfate were dissolved in the resultant solution to prepare an acidic mixed solution. The zinc oxide concentration was 4.1 mol/l. Separately, 6.4 kg of 99% sodium carbonate were dissolved in 60 l of pure water to prepare a 1 mol/l alkaline solution.

The acidic solution and the alkaline solution were fed separately from each other and simultaneously to a reaction tank by means of a flow-rate adjustable pump in such a manner that the molar ratio of zinc oxide to the alkaline solution is 1:2, to form a coprecipitate by neutralization. During this period of time, a continuous reaction was conducted under agitation at a high speed without particular heating while adjusting the pH value of the mixed solution to 6 to 8.

The slurry after the reaction, was subjected to repeated filtration and washing until the electrical conductivity of the filtrate reached 200 $\mu$S/cm or less to obtain a cake. The resultant cake was dried at 150° C. and fired at 400° C. in the air for 3 hrs to give an ultrafine composite oxide. The content of titanium oxide in the composite oxide was 8.34 parts by weight based on 100 parts by weight of zinc oxide.

This powdery composite oxide was surface treated with a silicone oil. The silicone oil used was one prepared by dissolving 135g of a silicone oil DC-3PA (purity: 10%) produced by Toray.Dow Corning Company, in 5 liters of toluene, agitating the resulting toluene solution of silicone oil for 5 minutes, thereafter adding 2.7 kg of zinc oxide to said toluene solution and then agitating for additional 30 minutes. The surface treated composite oxide was filtered off and dried at 120° C. to obtain a water-repellent powder which exhibited that the powder was fully coated with the silicone oil. Further, the amount of silicone oil coated was 0.5% by weight of the composite oxide.

The surface treated composite oxide powder was incorporated in an amount of 30 to 40% by weight in a polyester tesla, after which the mixture was subjected to dispersion together with glass beads for 1.5 hrs in a paint shaker, applied to an transparent polyethylene terephthalate sheet by means of a bar coater and then dried at 70° to 80° C. to prepare a transparent coating or film.

The transparent coating was measured for its transmittance in the region of visible lights (400 to 700 nm) by means of a turbidimeter manufactured by Nippon Denshoku Kogyo Co., Ltd., Japan. Further, the coating was measured for its transmittance in an ultraviolet region (380 nm) by means of a spectrophotometer manufactured by Hitachi Seisakusho Co., Ltd., Japan. The respective results are given in Table 2.

Further, the surface treatment of the composite oxide resulted in that the transmittance thereof somewhat decreased to 92.0% to 90.0%.

A coating which was the same as above was subjected to a 240-hour environmental resistance acceleration test at a temperature of 40° C. and a relative humidity of 90%. The transmittances of the coating in the visible light and ultraviolet regions were measured before and after the environmental resistance acceleration test, respectively, in the same manner as above with the results being as shown in Table 2.

EXAMPLE 2

The procedure of Example 1 was followed except that 300 g of n-decanoic acid and 30 l of methyl alcohol were substituted for 135 g of the silicone oil and 5 l of toluene, thereby to obtain a surface treated composite oxide powder and then prepare a transparent coating or film.

The coating so prepared was subjected to the same environmental resistance acceleration that as in Example 1 and then measured for its transmittances in the regions of visible lights and ultraviolet rays before and after said test, respectively, in the same manner as In Example 1. The results are as shown in Table 2.

EXAMPLE 3

The procedure of Example 2 was followed except that 300 g of lauric acid was substituted for 300 g of n-decanoic acid, thereby to obtain a surface-treated composite oxide powder and then prepare a transparent coating or film.

The coating so prepared was subjected to the same environmental resistance acceleration test as Example 1 and then measured for its transmittances in the visual light and ultraviolet regions before and after said test, respectively, in the same manner as in Example 1. The results are shown in Table 2.

Comparative Example 1

A comparative transparent coating was prepared from the non-surface treated composite oxide powder obtained in Example 1.

The comparative coating so prepared was subjected to the same environmental resistance acceleration test as in Example 1 and then measured for its transmittances in the visual light and ultraviolet regions before and after said test, respectively, in the same manner as in Example 1. The results are as shown in Table 2.

EXAMPLES 4–16

The procedure of Example 1 was repeated except that the kind(s) of metal oxide additive(s) and the amounts thereof added were varied as indicated in Table 1, thereby to obtain surface-treated ultrafine composite oxides.

These powdery composite oxides so obtained were each surface treated with n-decanoic acid or lauric acid in the same manner as in Examples 2–3, and a transparent coating was prepared from each of the thus obtained surface-treated composite oxides in the same manner as in Example 1.

The transparent coatings so prepared were subjected to an environmental resistance acceleration test as in Example 1 and then measured for their transmittances in the visual light region and the ultraviolet region before and after said test, respectively, in the same manner as in Example 1. The results are as shown in Table 2.

Comparative Example 2

A transparent coating was prepared directly from the non-surface treated composite oxide powder obtained in Example 4.

The coating was subjected to an environmental resistance acceleration test and measured for its transmittances in the visible light and ultraviolet ray regions before and after said test, respectively, in the same manner as in Example 1. The results are as shown in Table 2.

Comparative Example 3

A transparent coating was prepared directly from the non-surface treated composite oxide powder obtained in Example 13.

The coating was subjected to an environmental resistance acceleration test and measured for its transmittances in the visible light and ultraviolet ray regions before and after said test, respectively, in the same manner as in Example 1. The results are as shown in Table 2.

EXAMPLE 17

Eighteen (18) kilograms of 98% hydrated zinc sulfate, $ZnSO_4.7H_2O$, (about 5 kg in terms of zinc oxide) were dissolved in 30 l of pure water to obtain a solution in which 5.22 kg of 24% titanium sulfate (5% by weight of titanium based on zinc oxide) were then dissolved to obtain an acidic solution. The procedure of Example 1 was followed except that the acidic solution so obtained was used for mixture with an alkaline solution, thereby to obtain an ultrafine composite oxide.

The composite oxide powder so obtained was surface treated with n-decanoic acid in the same manner as in Example 2 to obtain a surface treated composite oxide powder from which a transparent coating was then prepared.

The coating was subjected to an environmental resistance acceleration test and measured for its transmittances in the visible light and ultraviolet ray regions before and after said test, respectively, in the same manner as in Example 1. The results are as shown in Table 2.

EXAMPLE 18

The procedure of Example 1 was followed except that there was used an acidic solution for mixture, which was prepared by adding 3.6 kg of 98% $ZnSO_4.7H_2O$ (about one kg in terms of zinc oxide) to an oxalic acid solution containing 17g of lanthanum (1.7% by weight of lanthanum based on zinc oxide), thereby to obtain an ultrafine composite oxide.

The composite oxide powder so obtained was surface treated with n-decanoic acid to obtain a surface treated composite oxide powder from which a transparent coating was then obtained in the same manner as in Example 2.

The coating was subjected to an environmental resistance acceleration test and measured for its transmittances in the visible light and ultraviolet; ray regions before and after said test, respectively, in the same manner as in Example 1. The results are as shown in Table 2.

EXAMPLE 19

The procedure of Example 18 was followed except that 1.72 g of cerium (0.17% by weight of cerium based on zinc oxide) was substituted for 17 g of lanthanum, thereby to obtain an ultrafine composite oxide.

The composite oxide powder so obtained was surface treated with n-decanoic acid to obtain a surface-treated composite oxide powder from which a transparent coating was then prepared in the same manner as in Example 2.

The coating was subjected to an environmental resistance acceleration test and measured for its transmittances in the visible light and ultraviolet ray regions before and after said test, respectively, in the same manner as in Example 1. The results are as shown in Table 2.

Table 1 indicates the metal oxide additives and the amounts thereof added as well as the surface treating agents and the amounts thereof coated, which were used in the above-described Examples and Comparative Examples.

TABLE 1

| Example Comp. Ex | Metal oxide additave (part by weight) (Ratio by weight of each additive to 100 parts by weight of zinc oxide) | | | | | | | Surface treating agent | |
|---|---|---|---|---|---|---|---|---|---|
| | $La_2O_3$ | $CeO_2$ | $Fe_2O_3$ | $CoO$ | $NiO$ | $TiO_2$ | $Al_2O_3$ | Kind of agent | Amount of agent coated *1 (% by weight) |
| Ex. 1 | | | | | | 8.34 | | Silicone Oil | 0.5 |
| Ex. 2 | | | | | | 8.34 | | n-decanoic acid | 0.5 |
| Ex. 3 | | | | | | 8.34 | | Lauric acid | 0.5 |
| Comp. Ex. 1 | | | | | | 8.34 | | — | — |
| Ex. 4 | | 0.2 | | | | | | n-decanoic acid | 0.5 |
| Ex. 5 | | 0.2 | | | | | | Lauric acid | 0.5 |
| Comp. Ex. 2 | | 0.2 | | | | | | — | — |
| Ex. 6 | 2.0 | | | | | | | n-decanoic acid | 0.5 |
| Ex. 7 | 2.0 | | | | | | | Lauric acid | 0.5 |
| Ex. 8 | | | 5.0 | | | | | n-decanoic acid | 0.5 |
| Ex. 9 | | | | 5.0 | | | | n-decanoic acid | 0.5 |
| Ex. 10 | | | | | 5.0 | | | n-decanoic acid | 0.5 |
| Ex. 11 | | | | | | | 9.45 | n-decanoic acid | 0.5 |
| Ex. 12 | | | | | | 8.34 | 9.45 | n-decanoic acid | 0.5 |
| Ex. 13 | | 0.2 | | | | 8.34 | | n-decanoic acid | 0.5 |
| Ex. 14 | | 0.2 | | | | 8.34 | | Lauric acid | 0.5 |
| Comp. Ex. 3 | | 0.2 | | | | 8.34 | | — | — |
| Ex. 15 | | 0.2 | | | | | 9.45 | n-decanoic acid | 0.5 |
| Ex. 16 | | 0.2 | | | | 8.34 | 9.45 | n-decanoic acid | 0.5 |
| Ex. 17 | | | | | | 8.34 | | n-decanoic acid | 0.5 |
| Ex. 18 | 2.0 | | | | | | | n-decanoic acid | 0.5 |
| Ex. 19 | | 2.0 | | | | | | n-decanoic acid | 0.5 |

*1: % by weight based on composite oxide before surface treatment

TABLE 2

| Example Comp. Ex. | 240-Hour Environmental Resistance Acceleration Test | | | |
|---|---|---|---|---|
| | Pretest transmittance of coating (%) | | Post-test transmittance of coating (%) | |
| | Visible light region 400–700 nm | Ultraviolet ray region 380 nm | Visible light region 400–700 nm | Ultraviolet ray region 380 nm |
| Ex. 1 | 90.0 | 5.0 | 90.0 | 5.0 |
| Ex. 2 | 92.0 | 5.0 | 88.0 | 8.0 |
| Ex. 3 | 92.0 | 5.0 | 88.0 | 10.0 |
| Comp. Ex. 1 | 92.0 | 5.0 | 76.0 | 19.0 |
| Ex. 4 | 93.0 | 3.5 | 93.0 | 4.0 |
| Ex. 5 | 93.0 | 3.5 | 93.0 | 4.0 |
| Comp. Ex. 2 | 93.0 | 3.5 | 81.0 | 18.0 |
| Ex. 6 | 90.0 | 7.0 | 89.0 | 8.0 |
| Ex. 7 | 90.0 | 7.0 | 88.0 | 8.0 |
| Ex. 8 | 82.0 | 6.5 | 80.0 | 6.5 |
| Ex. 9 | 83.0 | 5.9 | 81.0 | 6.0 |
| Ex. 10 | 83.0 | 6.7 | 80.0 | 8.0 |
| Ex. 11 | 94.0 | 10.0 | 93.0 | 11.3 |
| Ex. 12 | 92.0 | 5.0 | 91.0 | 10.0 |
| Ex. 13 | 91.0 | 3.0 | 91.0 | 8.5 |
| Ex. 14 | 91.0 | 3.0 | 90.0 | 9.0 |
| Comp. Ex. 3 | 91.0 | 3.0 | 88.0 | 22.0 |
| Ex. 15 | 93.0 | 3.5 | 92.0 | 6.0 |
| Ex. 16 | 90.0 | 2.9 | 90.0 | 5.0 |
| Ex. 17 | 92.0 | 6.0 | 90.0 | 7.0 |
| Ex. 18 | 92.0 | 8.0 | 90.0 | 10.0 |
| Ex. 19 | 90.0 | 3.0 | 90.0 | 4.0 |

As is apparent from Table 2, the surface-treated composite oxides prepared by surface treating the composite oxide with a silicone oil or a fatty acid and obtained in Examples 1–19, are improved in storage stability and can maintain their excellent ultraviolet screening effect and high transmittance in the region of visible lights over a long period of time. In contrast, the composite oxides (without surface treatment) obtained in Comparative Examples 1–3 exhibit their excellent ultraviolet screening effect and high transmittance in the region of visible lights in their early stages, but they are deteriorated in such superior properties as above with the lapse of time because of their unsatisfactory storage stability.

Effect of the Present Invention

As has been so far described, the ultraviolet screening, surface treated, composite oxides of the present invention not only have excellent ultraviolet screening capability and high visible-light transmittance, these two superior properties being well balanced with each other, but also can maintain the superior properties over a long period of time. Further, in eases where the surface treated composite oxides are incorporated in paints, cosmetics etc., they will never react with the matrix of the latter. In addition, the process of the present invention is capable of producing the above surface-treated composite oxides stably and uniformly on an industrial scale.

It is accordingly possible to appropriately use the ultraviolet screening composite oxides of the present invention as such for use in paints, cosmetics and the like.

What is claimed is:

1. An ultraviolet screening composite oxide consisting essentially of 100 parts by weight of zinc oxide and at least one member, incorporated therein, selected from the group consisting of oxides (1) to (7):
    (1) 0.001 to 5.0 parts by weight of lanthanum oxide,
    (2) 0.001 to 5.0 parts by weight of cerium oxide,
    (3) 1.0 to 10.0 parts by weight of iron oxide,
    (4) 1.0 to 10.0 parts by weight of cobalt oxide,
    (5) 1.0 to 10.0 parts by weight of nickel oxide,
    (6) 0.1 to 30.0 parts by weight of titanium oxide, and
    (7) 0.1 to 30.0 parts by weight of aluminum oxide,
the composite oxide being surface treated with one member selected from the group consisting of dimethylsilicone oil, methylphenyl-silicone oil, a cyclic silicone oil, a polyether silicone oil and methylhydrogensilicone oil, or one member selected from the group consisting of n-decanoic acid, caprilic acid, lauric acid, stearic acid, behenic acid and palmitic acid, linolic acid, linolenic acid and oleic acid in an amount of 0.05 to 10% by weight of said composite oxide.

2. An ultraviolet screening composite oxide according to claim 1, wherein said oxide is lanthanum oxide and is contained in an amount of 0.001 to 5.0 parts by weight based on 100 parts by weight of zinc oxide.

3. An ultraviolet screening composite oxide according to claim 1, wherein said oxide is cerium oxide and is contained in an amount of 0.001 to 5.0 parts by weight based on 100 parts by weight of zinc oxide.

4. An ultraviolet screening composite oxide according to claim 1, wherein said oxide is iron oxide and is contained in an amount of 1.0 to 10.0 parts by weight based on 100 parts by weight of zinc oxide.

5. An ultraviolet screening composite oxide according to claim 1, wherein said oxide is cobalt oxide and is contained in an amount of 1.0 to 10.0 parts by weight based on 100 parts by weight of zinc oxide.

6. An ultraviolet screening composite oxide according to claim 1, wherein said oxide is nickel oxide and is contained in an amount of 1.0 to 10.0 parts by weight based on 100 parts by weight of zinc oxide.

7. An ultraviolet screening composite oxide according to claim 1, wherein said oxide is titanium oxide and is contained in an amount of 0.1 to 30.0 parts by weight based on 100 parts by weight of zinc oxide.

8. An ultraviolet screening composite oxide according to claim 1, wherein said oxide is aluminum oxide and is contained in an amount of 0.1 to 30.0 parts by weight based on 100 parts by weight of zinc oxide.

9. The composite oxide according to claim 1 which contains at least one of said oxides (1) to (7) in the amount as defined in claim 1 and another of said oxides (1) to (7) in an amount lower than said amount defined in claim 1.

* * * * *